US006676596B2

(12) United States Patent

Erwin et al.

(10) Patent No.: US 6,676,596 B2
(45) Date of Patent: Jan. 13, 2004

(54) AI GUN WARMER

(75) Inventors: Kirk Steven Erwin, Rusk, TX (US); John Charles Etheredge, Roby, TX (US)

(73) Assignee: EM Tools, Inc., Rusk, TX (US)

( * ) Notice: Subject to any disclaimer, the term of this patent is extended or adjusted under 35 U.S.C. 154(b) by 0 days.

(21) Appl. No.: 09/832,536

(22) Filed: Apr. 11, 2001

(65) Prior Publication Data

US 2002/0151764 A1 Oct. 17, 2002

(51) Int. Cl.$^{7}$ .......................... A61B 17/43; A61D 7/00; F24C 7/10; H05B 3/34

(52) U.S. Cl. .......................... 600/35; 219/386; 219/528

(58) Field of Search ...................... 600/33–35; 119/174; 219/386, 387, 521, 528, 538, 552, 553; 222/146.5

(56) References Cited

U.S. PATENT DOCUMENTS

| | | | | | |
|---|---|---|---|---|---|
| 2,158,698 | A | | 5/1939 | Hettinger | 219/40 |
| 3,607,134 | A | | 9/1971 | McIntyre | 23/292 |
| 3,805,784 | A | * | 4/1974 | Alter | 128/235 |
| 3,904,037 | A | * | 9/1975 | Alter | 206/534 |
| 3,983,363 | A | * | 9/1976 | Alter | 219/521 |
| 4,007,367 | A | | 2/1977 | Rusteberg et al. | 219/385 |
| 4,493,700 | A | | 1/1985 | Cassou et al. | 604/55 |
| 5,380,988 | A | * | 1/1995 | Dyer | 219/548 |
| 5,512,730 | A | | 4/1996 | Spinello | 219/386 |
| 5,656,010 | A | | 8/1997 | Li et al. | 600/34 |
| 5,750,962 | A | * | 5/1998 | Hyatt | 219/528 |
| 5,884,006 | A | * | 3/1999 | Frohlich et al. | 392/339 |
| 5,932,129 | A | * | 8/1999 | Hyatt | 219/528 |
| 6,020,575 | A | | 2/2000 | Nagle et al. | 219/432 |
| 6,028,293 | A | | 2/2000 | Nagle et al. | 219/432 |
| 6,034,355 | A | * | 3/2000 | Naderi et al. | 219/387 |
| 6,071,231 | A | | 6/2000 | Mendoza et al. | 600/35 |

OTHER PUBLICATIONS

Select Sires, Inc., Handling of Frozen Semen Straws, Unknown Date, 4 Page Handout—Copy Enclosed.

Invention Disclosure Document, John Etheredge and Steve Erwin, A.I. Gun Warmer, Dec. 7, 1998, 4 Page Disclosure—Copy Enclosed.

* cited by examiner

*Primary Examiner*—Cary E. O'Connor
*Assistant Examiner*—Anuradha Ramana
(74) *Attorney, Agent, or Firm*—Larry Mason Lee

(57) ABSTRACT

A light weight, portable, temperature regulated enclosure for the pre-heating of artificial insemination guns and the transportation of loaded artificial insemination guns to the place of usage is disclosed. A flexible, planar heater using an etched electrically resistive metallic foil heating element and attached temperature sensor provides regulated heat to the interior of the enclosure.

6 Claims, 5 Drawing Sheets

AI GUN WARMER

BACKGROUND OF THE INVENTION a. Field of the Invention

The practice of artificial insemination of animals has made possible the improvement of the genetic quality of our herds of food stock and has become a widespread practice throughout the field of animal husbandry.

As a practical matter, artificial insemination of animals is accomplished by placing semen of the selected sire into an elongated plastic tube or "straw" and freezing the straw and its contents down to liquid nitrogen temperatures. The thus frozen straw and its contents can then be stored indefinitely for transport and use where and when desired. Upon arrival at the place of use, the first problem encountered by the prospective user, the purchaser of the semen, is to thaw the straw and its contents down to the liquid state without damaging the semen. Such damage usually makes itself apparent in a decreased activity level of the semen when used.

Once thawed down to the optimal temperature, the body temperature of the animal to be inseminated, the next or second problem encountered is maintaining the thawed semen at that optimal temperature until used. Temperature fluctuations cause degradation of the quality of the semen. Degradation of semen quality is typically measured in terms of decreased activity and thus decreased probability of a successful impregnation of the female animal to be artificially inseminated.

The problem of maintaining the thawed semen at optimal temperature until used has several parts. Firstly, the semen is loaded into an artificial insemination gun or syringe. The temperature of the artificial insemination gun must be preset to the optimal temperature, else loading the semen into the artificial insemination gun will cause a temperature fluctuation in the syringe. The temperature of the artificial insemination gun must be pre-set to the optimal temperature, else loading the semen into the artificial insemination gun will cause a temperature fluctuation in the semen as the semen and the artificial insemination gun exchange heat to reach a common temperature.

Secondly, the loaded artificial insemination gun must transported from the place of the semen thaw to the place of use. In order to maintain optimal temperature of the semen while it is being transported, the loaded artificial insemination gun must be enclosed and protected from the weather and the enclosure must be both portable and temperature regulated.

Accordingly, the present invention is related generally to the field of apparatus for maintaining biological materials, more particularly fluids such as blood, semen, etc., at optimal temperatures in order to preserve viability during transport or storage.

The present invention is related more particularly to the field of apparatus for transporting thawed animal semen and maintaining such thawed semen at optimal temperature for subsequent use in insemination of an animal.

Yet more particularly, the present invention is related to apparatus useful in maintaining at a temperature slightly below the body temperature of the animal species of origin of the thawed animal semen that has been stored in frozen state by application of liquid nitrogen; and maintaining such thawed, now liquid, animal semen at such optimal temperature, which is slightly below the body temperature of the animal, until used.

b. Description of the Prior Art

Relevant prior art is known to include various tissue sample holders, semen thawing systems, temperature controlled containers for transport of biological materials, and an apparatus utilized to hold thermoplastic hypodermic syringes during sterilization.

U.S. Pat. No. 3,607,134, McIntyre, discloses a sample holder for maintaining blood samples at a pre-selected temperature. The device disclosed is not adapted to the use intended for the instant invention and accordingly does not provide for enclosure of the tissue sample holders in order to protect same from the weather, does not provide an interior enclosure shape which urges the lower end of the tissue sample holders into a compact area, and does not disclose a temperature control means useful during transport of the tissue sample holders.

U.S. Pat. No. 4,007,367, Rusteberg, discloses a portable holding chamber for thawed semen straws which is temperature controlled. The holding chamber disclosed depends for its energy source upon connection to a thawing unit and could therefore be inconvenient unless the thawing takes place within close proximity to the place of the semen use. Additionally, disconnection of the energy source also disconnects the temperature regulation circuitry of the disclosed device. Additionally, the holding chamber's design provides for separate carriage of the semen straws and the "sheaths" for the artificial insemination guns, that is, the holding chamber anticipates that the semen straws will be loaded into the artificial insemination guns at the point of usage which may be disadvantageous if the weather is inclement. Finally, the holding chamber, in use, is filled with water as a heat retention medium which adds to the weight of the holding chamber and detracts from the ease of transportability.

U.S. Pat. No. 5,512,730, Spinello, discloses a container in which thermoplastic hypodermic syringes may be placed for sterilization. The container provides a semi-conical interior surface which forces the needles and needle ends of the inserted hypodermic syringes into a close proximity to one another. However, being designed for sterilization, the container is not designed to be portable nor is the container temperature regulated about a chosen temperature.

U.S. Pat. No. 6,028,293, Nagle, discloses a temperature-controlled container for transporting biologic tissue. Being specialized for the transport of human tissue, the container disclosed provides for a shock resistant, transportable, temperature controlled container whose interior is shaped to contain a nutrient rich broth to sustain the life of the human tissue. The container disclosed is not suitable for the transport of loaded artificial insemination guns due to the shape and dimensions of its interior annular chamber and to its preferred construction material, closed cell polymers. The use of closed cell polymers is optimal for the disclosed objects of shock resistance and long term (120 hour) temperature stability, but fails to provide protection against breaking or bending for an elongated object such as a loaded artificial insemination gun.

SUMMARY OF THE INVENTION

The instant invention is of a portable, temperature controlled enclosure suitable for use in transporting a loaded artificial insemination gun from the point of thawing to the place of use. The numerous problems noted in the prior art of portable, temperature controlled enclosures are addressed in the instant invention and the result is a highly effective, easily transportable (can be clipped to and carried on the belt) enclosure which is uniquely suited to the preservation of live, active semen within the straw loaded into an artificial insemination gun.

Accordingly, it is an object of the instant invention to provide a portable, temperature controlled enclosure suitable for use in animal tissue, embryo, and semen transport.

It is another object of the instant invention to provide a portable, temperature controlled enclosure suitable for use in animal tissue, embryo, and semen transport with an interior enclosure shape which urges the lower end of the tissue sample holders into a compact area.

It is yet another object of the instant invention to provide a portable, temperature controlled enclosure suitable for use in animal tissue, embryo, and semen transport which is lightweight and suitable for transporting a loaded artificial insemination gun.

It is yet another object of the instant invention to provide a temperature controlled enclosure suitable for use in animal tissue, embryo, and semen transport which is battery operated.

It is yet another object of the instant invention to provide a temperature controlled enclosure suitable for use in animal tissue, embryo, and semen transport which provides a lightweight, rapid temperature response heater in an energy conserving configuration.

It is yet a further and final object of the instant invention to provide a temperature controlled enclosure suitable for use in animal tissue, embryo, and semen transport which provides protection against breaking or bending for an elongated object such as a loaded artificial insemination gun.

DESCRIPTION OF NUMERIC REFERENCES

1. the instant invention
3. outer shell
5. pocket on exterior of outer shell
7*a*. top half of zipper on outer shell
7*b*. bottom half of zipper on outer shell
9. zipper on pocket on exterior of outer shell
11. clear vinyl window through material of pocket
12. on-off switch
13. upper layer of insulation
15. lower layer of insulation
17. heater
19. heater pocket on interior of inner shell
21. inner shell
23. tapered liner or pocket
25. fold line
27. zipper
28. opening of tapered liner
29. foot of tapered liner
30. artificial insemination gun
32. semen straw
34. finger grip
36. plunger of artificial insemination gun
38. barrel of artificial insemination gun
40. adhesive backed aluminum foil
42. temperature sensor
44. electrical connection to temperature sensor
46. heater power lead
47. heater power lead
50. aluminum foil
51. silicone impregnated fiberglass cloth
52. silicone impregnated fiberglass cloth
54. chemically milled electrically resistive metallic foil
56. silicone impregnated fiberglass cloth Note: those reference numbers not appearing in the above listing are not used.

BRIEF DESCRIPTION OF THE DRAWINGS

While the novel features of the instant invention are set forth with particularity in the appended claims, a full and complete understanding of the invention can be had by referring to the detailed description of the preferred embodiment(s) which are set forth subsequently, and which are as illustrated in the accompanying drawings, in which:

DESCRIPTION OF THE PREFERRED EMBODIMENT(S)

To better understand the instant invention and the advantages it offers, it is first necessary to briefly review the currently used process and techniques for transporting thawed semen from the thawing tank to the place of insemination.

Typically, semen is available for purchase packaged in ½ milliliter, 5 inch long French Straws. Each straw 32 is clipped onto a metal cane and the cane is attached to a goblet which is immersed in liquid nitrogen. Straws 32 are typically made of transparent plastic material, and might be referred to as a pipette in a laboratory setting.

When the straw 32 is delivered to a customer (rancher or farmer), the cane is transferred to a liquid nitrogen tank canister at the customer's place of business. The transfer from the vendor's liquid nitrogen tank to the customer's liquid nitrogen tank is done rapidly in order to avoid thawing the semen in the straws 32. The customer is advised to leave the straws 32 immersed in a goblet with liquid nitrogen and not take them out of the goblet until needed for use.

When the time for use of the semen arrives, the customer removes the straws 32 individually from the goblet and places them into a container of thaw water which is preheated to the optimal temperature, a temperature slightly below the animal's body temperature (95 degrees for cattle) to thaw and stabilize at the desired temperature. The liquid nitrogen canister should be re-closed immediately after extraction of a straw 32 from the goblet contained within the canister so that the other straws 32 being held by the goblet don't begin to thaw. Temperature fluctuation of the straw 32, particularly partial thawing and re-freezing causes severe damage to the semen within the straw 32 and may render it worthless.

Figure 3:
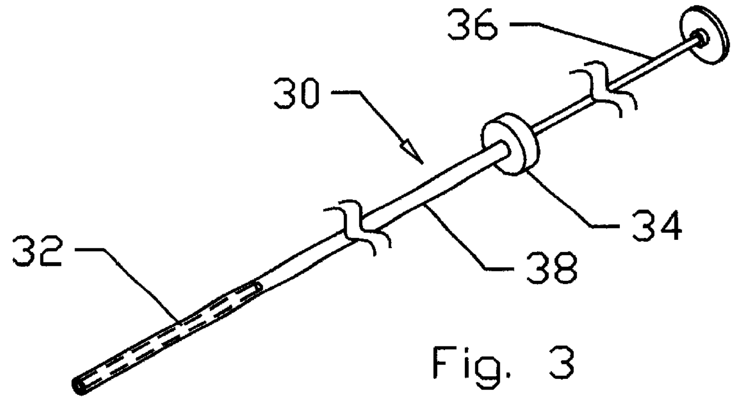
FIG. 3 is a partially cut away perspective view of a typical artificial insemination gun with straw loaded.

The straw 32, once thawed, must then be inserted into an artificial insemination gun 30 (see FIG. 3) and transported to the place of use, typically outside in a barn or pen setting near where the animals are usually kept. The loaded, thawed straw 32 is plugged with cotton wadding a one end, is crimped at the other end, and will exhibit an air bubble at the crimped end of the straw 32 if properly thawed.

The artificial insemination gun 30, or syringe, is loaded by withdrawing the plunger 36 of the artificial insemination gun 30 from the barrel 38 by approximately 6½" and then placing the end of the straw 32 containing the cotton plug into the end of the artificial insemination gun 30. The thawed semen straw 32 is loaded into the barrel 38 of the artificial insemination gun 30 cotton stuffed end first.

Transportation of the loaded artificial insemination gun 30 to the place of use is often accomplished by placing the loaded artificial insemination gun 30 inside the shirt or clothing of the person transporting the artificial insemination gun 30. The transporter's body heat then supplies the heat regulation afforded to the loaded artificial insemination gun 30 during its trip from the thaw water container to the place of use. Variation of the temperature above and below a stable 95 degrees (for example, other temperatures will apply for other animals) will degrade the quality of the semen within the straw. "Degrade" means lower the activity level and thus the probability of a successful artificial insemination of the female animal.

The AI Gun Warmer 1, while accomplishing the previously stated objects of the invention, additionally addresses two of the most significant problems routinely encountered in the previously described process of getting active, live semen from the thaw water to the point of injection into the female animal. Those two problems are 1) pre-warming the artificial insemination gun 30 so that the thawed semen within the straw 32 does not undergo a temperature change upon loading of the straw 32 into the artificial insemination gun 30; and 2) maintaining the artificial insemination gun 30 and semen within the loaded straw 32 at a constant temperature as long as the artificial insemination gun 30 is enclosed within AI Gun Warmer.

Figure 1:
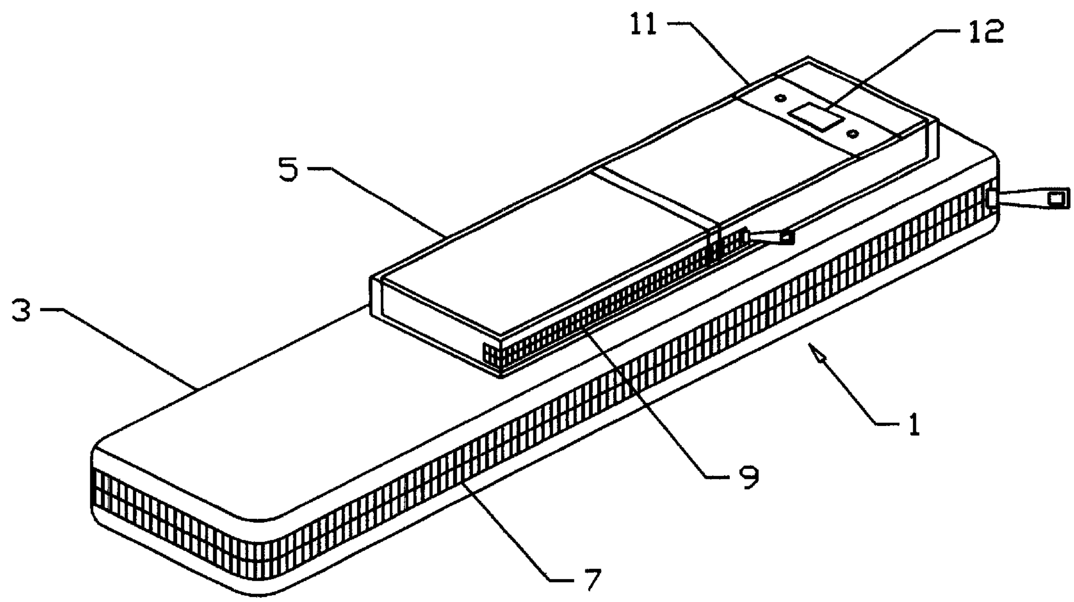
FIG. 1 is a perspective view of the exterior of the instant invention in its closed position.

In the preferred embodiment, the AI Gun Warmer 1 is seen in exterior view in FIG. 1 to provide an outer shell 3 of single piece construction with a zipper 7 fastening the edges of the outer shell 3 together. The outer shell 3, in the preferred embodiment is made of sturdy, waterproof cloth. Clearly, a solid, hinged outer shell 3 could be constructed with necessary gaskets, seals and fasteners taking the place of the zipper 7; however, the preferred embodiment strives for low cost practicality. Additionally, the exterior view, FIG. 1, of the AI Gun Warmer 1 discloses a pocket 5 closed by a zipper 9. Within the pocket 5, which is attached to the exterior of the outer shell 3, is located the battery and electronic circuitry that controls the energy transfer to the interior of the AI Gun Warmer 1. Also, FIG. 1 discloses a clear vinyl window 11 in the pocket 5 through which battery power indicators, temperature indicators, and the like provided by the electronic circuitry contained within the pocket 5.

Figure 2:
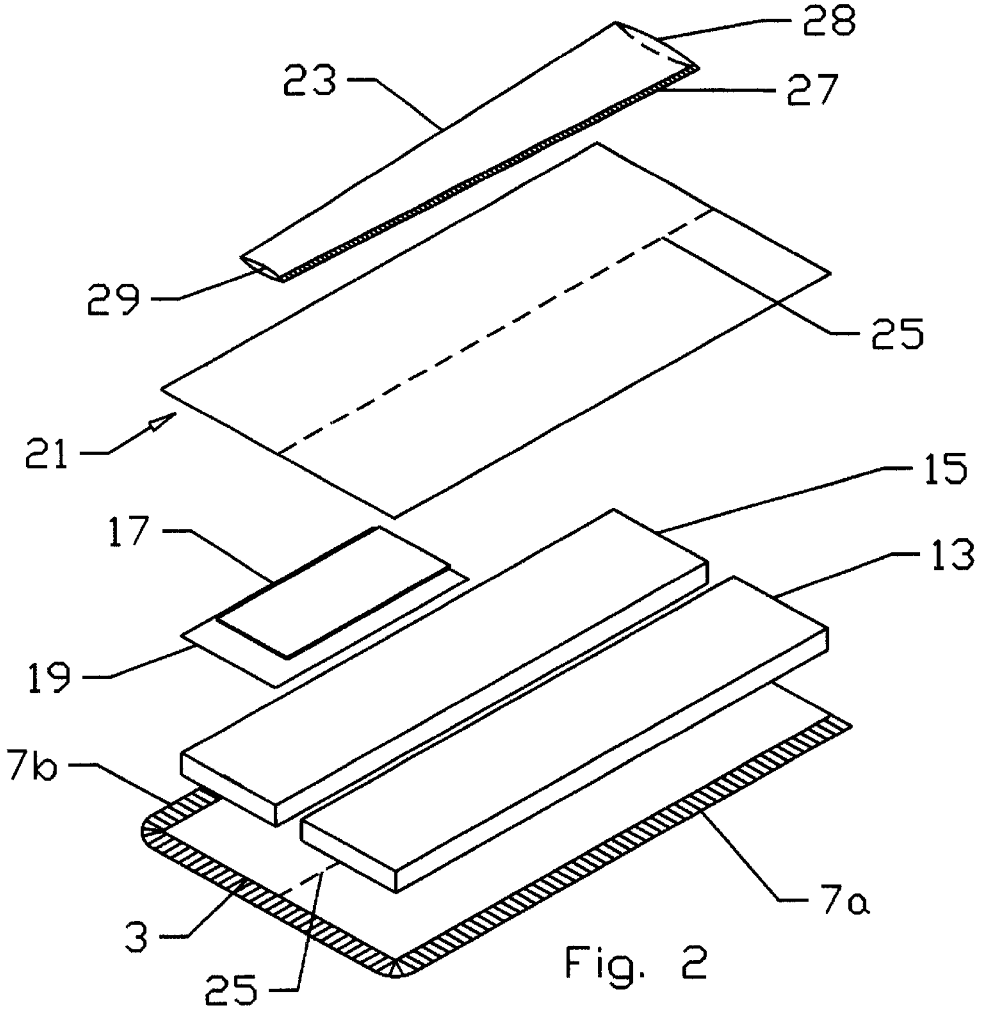
FIG. 2 is a perspective view of the components of the instant invention.

FIG. 2 depicts the major components of the AI Gun Warmer 1 which are inside of the outer shell 3. In FIG. 2, the zipper 7 is depicted in two parts as the upper half of the zipper 7*a* and the lower half of the zipper 7*b*. The major components are the upper layer of insulation 13, the lower layer of insulation 15, the heater 17, the heater pocket 19, the inner shell 21, and the tapered liner 23. Note that the major components, as depicted in FIG. 2, are spread out in a pre-assembly fashion and upon assembly the outer shell 3, upper layer of insulation 13, and the inner shell 21 are intended to be folded over the tapered liner 23 along the fold line 25, permitting the two halves of the zipper, 7*a* and 7*b*, to connect, combining into zipper 7 as depicted in FIG. 1.

The upper layer of insulation 13 and the lower layer of insulation 15 may be of any solid insulating material. In the preferred embodiment a closed cell polymer that imparts substantial body or stiffness to the AI Gun Warmer 1 is used. This imparts shape to the AI Gun Warmer 1 and provides protection for, as well as insulation to, the artificial insemination gun(s) 30 that will be placed into the tapered liner 23 for transport from the place of thawing to the place of use. Further, the closed polymer material provides sufficient flexibility that the insulating material of the upper layer of insulation 13 and the lower layer of insulation 15 may be said, when squeezed together by zipping up the tightly fitting outer shell 3, to enclose the heater 17 and the tapered liner 23. Enclosing the heater 17 and the tapered liner 23 with insulating material causes heat loss from the heater 17, and/or from an artificial insemination gun 30 being transported, to the outside environment to be minimal.

The inner shell 21 is made of water-proof flexible material and has attached to its bottom side a heater pocket 19 into which the heater 17 fits. The inner shell 21 must consist of material that is readily heat conductive. In the preferred embodiment, the inner shell 21 is made of a strong, durable water-proof cloth. This choice of materials provides the desirable characteristics of light weight, water-proof, easy heat transfer, and low cost. The inner shell 21 is connected to the outer shell 3, in the preferred embodiment the connection is made by stitching.

The tapered liner 23 or sheath for the receipt of the artificial insemination gun 30 is manufactured of lightweight, water-proof, heat conductive material, and provides a zipper 27 along its length to facilitate opening and cleaning. In the preferred embodiment, the tapered liner 23 is made of durable water-proof cloth, although numerous other materials, whether flexible or not, could be satisfactorily substituted. In a second embodiment, the tapered liner 23 is a hard shell of rigid plastic material with the capability of providing substantial additional protection to the artificial insemination gun(s) carried within. The shape of the tapered liner 23 is such that the opening 28 is wider than the foot 29. The tapered liner 23 is held in position by attachment, stitching in the preferred embodiment, to the inner shell 21. The foot 29 of the tapered liner 23 is oriented toward the end of the outer shell 3 which is completely zipped when assembled and closed for transport of an artificial insemination gun 30.

In another embodiment of the instant invention, the tapered liner 23 is dispensed with and the sheath for the receipt of the artificial insemination gun 30 is simply a cavity formed within the upper layer of insulation 13 and/or the lower layer of insulation 15.

In yet another embodiment of the instant invention, the tapered liner 23 or sheath is made of insulating material, the heater 17 is located within the tapered liner 23, and the upper layer of insulation 13 and the lower layer of insulation 15 are dispensed with.

Figure 4:
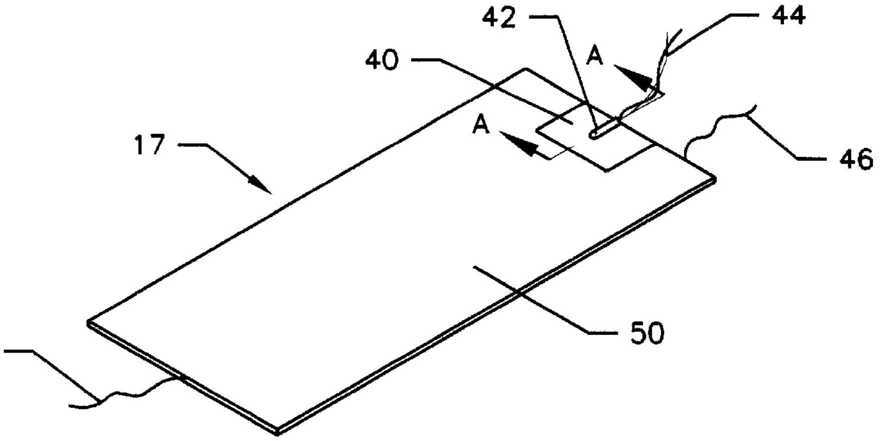
FIG. 4 is a perspective view of the top of the heater and temperature sensor.
Figure 5:
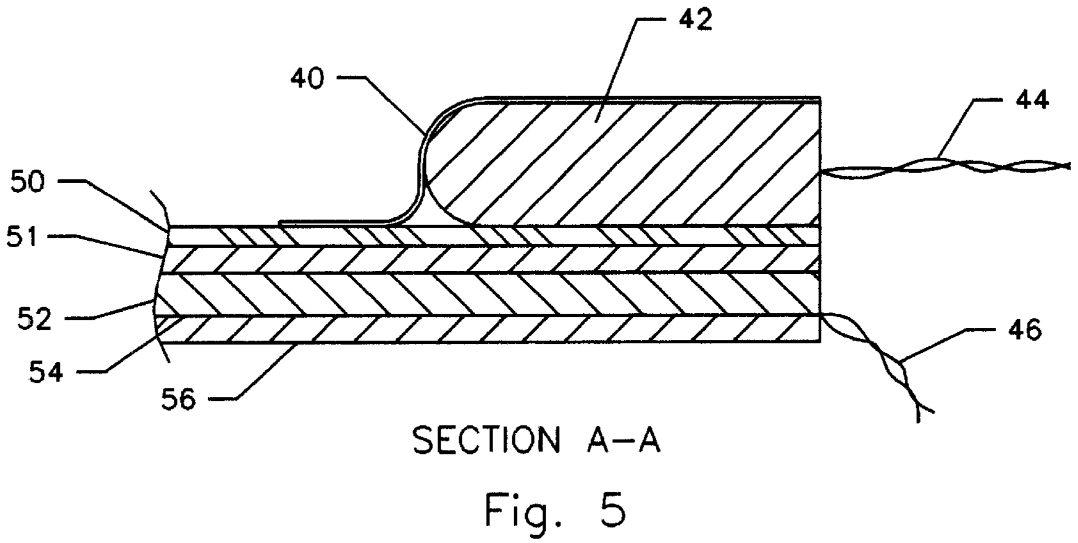
FIG. 5 is a sectional view of the temperature sensor and heater taken along the line A—A.

The heater 17, which is depicted in detail in FIGS. 4 and 5, is designed to provide the required temperature stability, is light weight, and conserve energy to decrease battery usage and thus lengthen the duration of field use between battery charges. Battery charges are accomplished through use of standard external power sources, such as a 15V DC power supply that connected to a standard AC source. An external power source, which may be an auto battery or a 15V DC power supply, may if available be used instead of the battery of the instant invention to provide energy for the electronic circuitry and the heater 17. The heater 17 is a chemically milled (etched) electrically resistive metallic foil 54 (which is the heating element of the heater 17) vulcanized between two plies of silicone rubber impregnated fiberglass cloth (references nos. 52 and 56) with insulated lead wires 46 and 47 attached centrally to the heating element and with a piece of aluminum foil 50 vulcanized to the surface of the silicone rubber impregnated cloth 52 using an additional ply of silicone impregnated fiberglass cloth 51. The heater 17 provides a temperature sensor 42, which may be either electronic or mechanical, which in the preferred embodiment is attached to a layer of aluminum foil 50 by adhesive backed aluminum foil 40. The materials used in the heater 17 were chosen for their heat conductive characteristics, flexibility, light weight and small volume. The temperature sensor 42 has attached electrical connections 44 which put the temperature sensor 42 in electrical communication with the electronic circuitry contained in the pocket 5 exterior to the outer shell 3. The etched electrically resistive metallic foil 54 used as a heating element has attached electrical connections 46 and 47 which put the heating element in electrical communication with the electronic circuitry contained in the pocket 5 exterior to the outer shell 3. The heater 17, in combination with the electronic circuitry contained in the pocket 5 exterior to the outer shell 3, maintain the temperature within the tapered liner 23 within very close tolerances.

Figure 6:
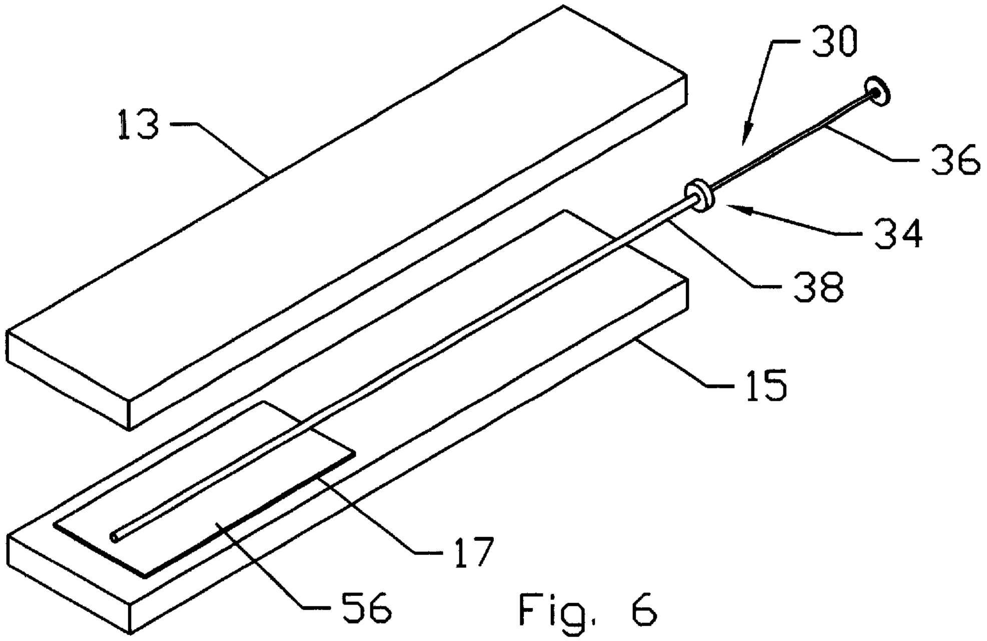
FIG. 6 is a perspective view of invention components depicting the artificial insemination gun in position (without a tapered liner) above the heater.
Figure 7:
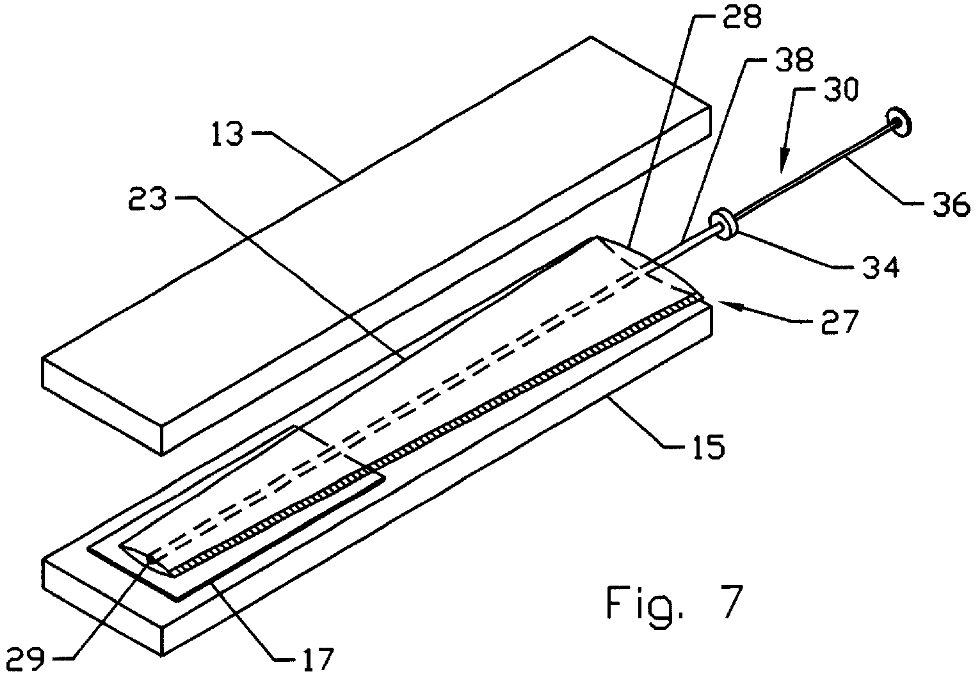
FIG. 7 is a perspective view of invention components depicting the artificial insemination gun in position (with tapered liner in position) above the heater.

FIG. 6 depicts the relative positions during use as an enclosure to transport an artificial insemination gun 30, of the top insulating layer 13, the artificial insemination gun 30, the heater 17, and the lower insulating layer 15. FIG. 6 purposely omits the tapered liner 23 for clarity. As shown in FIG. 6, the heater 17 is in heat conductive communication primarily with only the lower 6½" of the barrel 38 of the artificial insemination gun 30. As the semen straw 32 is approximately 5" long, the heater 17 is positioned to slightly overlap, both top and bottom, of the semen straw 32 and thus is responsive to and applies heat to the semen straw 32 rather than to the artificial insemination gun 30 in gross. This placement of the heater 17 relative to the semen straw 32 and the smaller area over which heat is sensed, regulated and applied, provides the advantages of closer tolerance temperature regulation of the semen within the straw 32 and conservation of energy by not applying heat to a larger area. FIG. 7 depicts the same view as FIG. 6, but with the tapered liner 23 shown in position and being used as a sheath for the artificial insemination gun 30.

Figure 8:
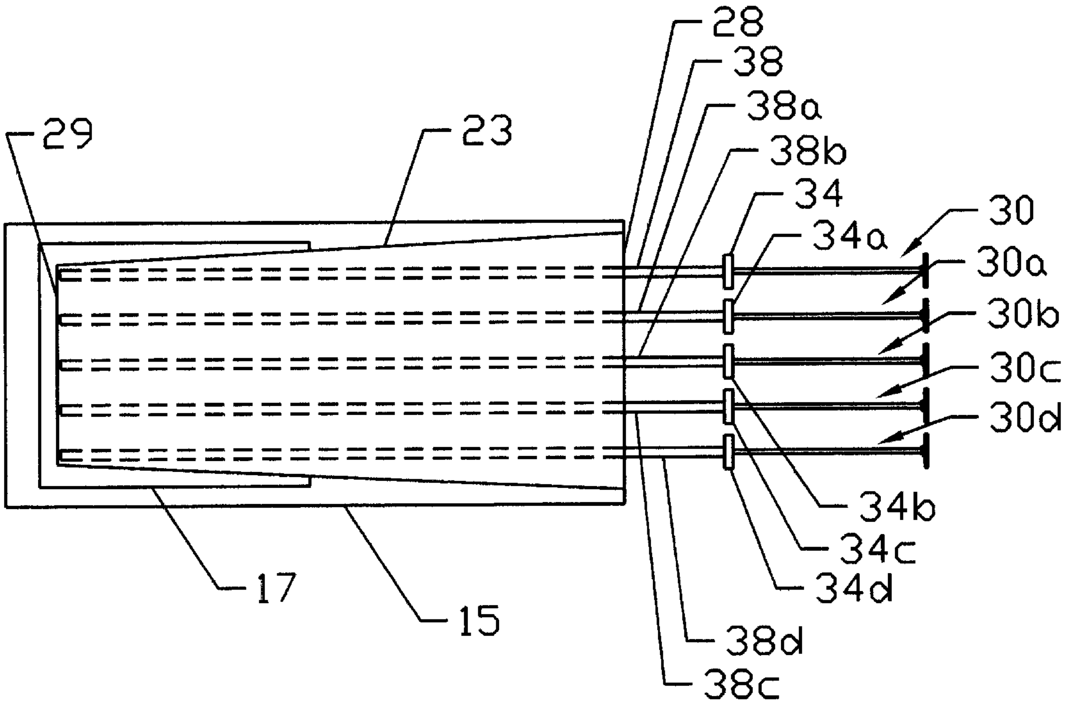
FIG. 8 is a plane view of the invention depicting several artificial insemination guns in position within the tapered liner.

FIG. 8 is a top plane view of the AI Gun Warmer 1 taken just above the tapered liner 23. As seen in FIG. 8, the tapered liner 23 serves to force the ends of the barrels 38, 38*a*, 38*b*, 38*c*, 38*d* of the artificial insemination guns 30, 30*a*, 30*b*, 30*c*, 30*d* into close proximity in foot 29 of the tapered liner 23 which is the area heated by the heater 17. At the same time, the opening 28 of the tapered liner 23 is wide enough to accommodate and provide spacing for the finger grips 34, 34*a*, 34*b*, 34*c*, 34*d* of five artificial insemination guns 30, 30*a*, 30*b*, 30*c*, 30*d*. The tapered liner 23 may, in some embodiments, provide guides for the insertion of each of the artificial insemination guns 30 to be transported therein. Additionally, the tapered liner 23 may, in some embodiments, be a solid material, as for example a hard plastic and provide hinges, seals, gaskets, and latches to accommodate the need for opening and cleaning after use.

In operation, the preferred embodiment of the AI Gun Warmer 1 is utilized by switching the on-off switch 12 which is accessible through the transparent plastic window 11 to the On position thereby applying energy to the electronic circuitry which, in turn, controls the energy to the electrical connections 44, 46 and 47 which lead to the temperature sensor 42 and to the etched electrically resistive metallic foil 54, respectively.

After applying power to the heater 17 the user monitors the temperature of the heater 17 by observing the temperature indicator which is provided by the electronic circuitry contained within the pocket 5, which temperature indicator is observable through the transparent window 11. Once the temperature of the temperature sensor 42 stabilizes at the value preset for the AI Gun Warmer 1, the user places the empty artificial insemination guns 30 that he intends to load with semen straws 32 into the opening 28 of the tapered liner 23 and pushes the empty artificial insemination guns 30 down into the tapered liner 23 until the barrels 38 of the artificial insemination guns 30 reach the foot 29 of the tapered liner 23. This action places the ends of the barrels 38 of the artificial insemination guns 30 into the heating zone or area of the tapered liner 23 to which heat is transferred by the heater 17.

Once the temperature of the artificial insemination guns 30 are stabilized and the semen straws 32 are thawed and temperature stabilized, then the artificial insemination guns 30 are withdrawn, one by one, from the AI Gun Warmer 1 for loading. At the time of loading both the artificial insemination gun 30 being loaded and the semen straw 32 have been temperature stabilized, by the AI Gun Warmer 1 and the water thaw, respectively, to the same temperature. To load the thawed semen straw 32, the plunger 36 of the artificial insemination gun 30 is withdrawn from the barrel 38 by approximately 6½", the thawed semen straw 32 is then loaded into the barrel 38 of the artificial insemination gun 30 cotton stuffed end first.

Following the loading of the semen straw 32 into the artificial insemination gun 30, the artificial insemination gun 30 is reinserted into the AI Gun Warmer 1 by slipping the artificial insemination gun 30 into the tapered liner 23 barrel 38 first and pushing the artificial insemination gun 30 down into the tapered liner 23 until the end of the barrel 38 makes contact with the foot 29 of the tapered liner 23 thereby placing the portion of the barrel 38 in which the semen straw 32 rests into the heating zone of the heater 17. The described process of removing an artificial insemination gun 30 from the tapered liner 23, loading it, and replacing it within the tapered liner 23 should be repeated as necessary until all artificial insemination guns 30 which are to be transported to the place of use have been secured within the AI Gun Warmer 1.

The loaded artificial insemination guns 30 to be transported should remain in position within the temperature controlled environment provided by the AI Gun Warmer 1 until the loaded artificial insemination gun 30 is removed from the tapered liner 23 for use.

Following use, the discharged artificial insemination guns 30 are withdrawn from the AI Gun Warmer 1, the on-off switch 12 is switched to the off position, disconnecting power from the heater 17 and all equipment including the AI Gun Warmer 1 must be cleaned for storage and subsequent periods of use. To clean the AI Gun Warmer 1, the zipper 7 is opened giving access to the tapered liner 23. The zipper 27 of the tapered liner 23 is then opened and the inside of the tapered liner 23 is washed out or cleaned. After cleaning the interior of the tapered liner 23 and permitting such interior to dry, the zipper 27 is closed, the zipper 7 is closed, and AI Gun Warmer 1 is stored for subsequent use.

While the preferred embodiments of the instant invention have been described in substantial detail and fully and completely hereinabove, it will be apparent to one skilled in the art that numerous variations of the instant invention may be made without departing from the spirit and scope of the instant invention, and accordingly the instant invention is to be limited only by the following claims.

I claim:

1. A temperature controlled enclosure suitable for transporting artificial insemination guns having barrels loaded with thawed semen straws which comprises a portable energy source, temperature regulation circuitry, a heater, insulating material and a sheath, wherein
- said portable energy source provides energy to said heater as required by said temperature regulation circuitry,
- said insulating material surrounds said sheath,
- said sheath is comprised of heat conductive materials,
- said sheath is shaped to receive the barrels of artificial insemination guns and guide them into close proximity within a small area at the bottom of said sheath,
- said heater is positioned between said insulating material and said sheath, and
- said heater provides heat to said small area;

whereby
- said artificial insemination guns are positioned within said sheath, and
- the ends of said barrels of said artificial insemination guns are kept at a regulated temperature.

2. The temperature controlled enclosure of claim 1 wherein the heater provides a heating element comprised of a sheet of an etched electrically resistive metallic foil.

3. The temperature controlled enclosure of claim 1 wherein said sheath comprises a cavity within said insulating material.

4. A temperature controlled enclosure suitable for transporting artificial insemination guns having barrels loaded with thawed semen straws which comprises a portable energy source, temperature regulation circuitry, a heater, and a sheath made of insulating material, wherein
- said portable energy source provides energy to said heater as required by said temperature regulation circuitry,
- said sheath is shaped to receive the barrels of artificial insemination guns and guide them into close proximity within a small area at the bottom of said sheath,
- said heater is positioned within said sheath, and
- said heater provides heat to said small area;

whereby
- said artificial insemination guns are positioned within said sheath, and
- the ends of said barrels of said artificial insemination guns are kept at a regulated temperature.

5. The temperature controlled enclosure of claim 4 wherein the heater provides a heating element comprised of a sheet of an etched electrically resistive metallic foil.

6. The temperature controlled enclosure of claim 5 wherein said sheath comprises a cavity within said insulating material.

* * * * *